United States Patent [19]

Houlihan et al.

[11] Patent Number: 4,673,672

[45] Date of Patent: Jun. 16, 1987

[54] SUBSTITUTED-[HYDROXY(TETRAHYDRO)-5-OXO-(2- AND 3-FURANYL OR 2-THIENYL)ALKOXYPHOSPHINYLOXY]-ALKANAMINIUM HYDROXIDE, INNER SALT OXIDES

[75] Inventors: William J. Houlihan, Mountain Lakes; Mark L. Lee, Lake Hopatcong, both of N.J.

[73] Assignee: Sandoz Pharmaceuticals Corp., E. Hanover, N.J.

[21] Appl. No.: 875,166

[22] Filed: Jun. 17, 1986

Related U.S. Application Data

[63] Continuation-in-part of Ser. No. 792,095, Oct. 28, 1985, abandoned.

[51] Int. Cl.[4] .................. A61K 31/665; A61K 31/67; C07F 9/141
[52] U.S. Cl. ........................................ 514/95; 514/99; 549/8; 549/218; 549/222
[58] Field of Search .......................... 549/8, 218, 222; 514/95, 99

[56] References Cited

FOREIGN PATENT DOCUMENTS 57045 8/1982 European Pat. Off. .
103877 3/1984 European Pat. Off. .
165395 10/1982 Japan .

OTHER PUBLICATIONS

Nippon Soda Co., Chemical Abstracts, vol. 102 (1985) 221143a

*Primary Examiner*—Richard L. Raymond
*Attorney, Agent, or Firm*—Gerald D. Sharkin; Robert S. Honor; Joseph J. Borovian

[57] ABSTRACT

The invention discloses substituted 2-[hydroxy(tetrahydro)-5-oxo-(2- and 3-furanyl or 2-thienyl) alkoxyphosphinyloxy]-alkanaminium hydroxide inner salt-4-oxides useful as anti-tumor agents, pharmaceutical compositions containing said compounds as an active ingredient thereof and a method of using such compositions for treating tumors.

25 Claims, No Drawings

SUBSTITUTED-[HYDROXY(TETRAHYDRO)-5-OXO-(2- AND 3-FURANYL OR 2-THIENYL)ALKOXYPHOSPHINYLOXY]-ALKANAMINIUM HYDROXIDE, INNER SALT OXIDES

This application is a continuation-in-part of U.S. patent application Ser. No. 792,095, filed Oct. 28, 1985, now abandoned.

The present invention relates to certain substituted 2-[hydroxy(tetrahydro)-5-oxo-(2- and 3-furanyl or 2-thienyl)alkoxyphosphinyloxyl-alkanaminium hydroxide inner salt-4-oxides, and to their use as anti-tumor agents. The invention also relates to pharmaceutical compositions containing the aforementioned compounds as an active ingredient thereof and to the method of using such compositions for treating tumors.

Leukemia, as well as other malignancies of unknown origin including ascitic tumors, has occupied the attention of research organizations for many years and until most recently without appreciable success. Today, many types of tumors can be effectively treated with drugs. In this connection, U.S. Pat. No. 4,119,714 discloses certain etherlysolecithins useful in influencing and controlling the interfacial properties of cell membranes, U.S. Pat. No. 4,393,052 discloses novel anthracycline glycosides useful in treating certain tumors, U.S. Pat. No. 4,393,064 discloses the uses of 10-deazaminepterin treating leukemia and ascitic tumors, U.S. Pat. No. 4,396,553 is directed to tetrahydronaphthalene and indane compounds which are useful as tumor inhibiting agents and U.S. Pat. No. 4,426,525 discloses certain tridecyloxy or tetradecyloxy propane derivatives useful in inhibiting the multiplication of tumor cells. In addition, Belgian Pat. Nos. 854,269 and 854,270 disclose anti-tumor lysolecithin compositions effective against Ehrlich's Ascites methylcholanthrene-induced tumors and myelomas.

The essence of the present invention is the discovery that certain substituted 2-[hydroxy(tetrahydro)-5-oxo-(2- and 3-furanyl or 2-thienyl)alkoxyphosphinyloxyl]-alkanaminium hydroxide inner salt oxides of formula I,

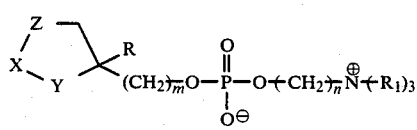

where
R is n-$C_{14}$-$C_{18}$ alkyl; $CH_2OR_2$, where $R_2$ is n-$C_{14}$-$C_{18}$ alkyl; or $CH_2CH_2OR_2$, where $R_2$ is as defined above;
$R_1$ is n-$C_1$-$C_3$ alkyl;
X is —$CH_2$—, C=O or —O—;
Y is —$CH_2$—, —O— or —S—;
Z is —$CH_2$— or C=O;
m is an integer 1 or 2;
and
n is an integer 2 to 8; with the provisos that: (1) when X is —O—, Y is —$CH_2$—; and (2) when Y is —O— or —S— and X is —$CH_2$— or C=O, Z is —$CH_2$—;
are useful as anti-tumor agents.

Included among the compounds of formula I are the compounds of subclass Ia:

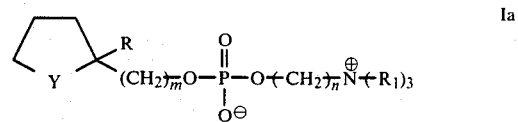

where Y is —O— or —S—; and R, $R_1$, m and n are as defined above.

The preferred compounds of subclass Ia are compounds of the formula Ia':

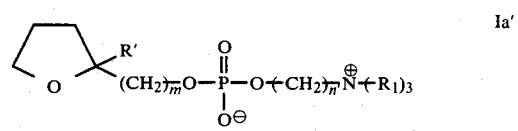

where
R' is n-$C_{16}$-$C_{18}$ alkyl; $CH_2OR'_2$, where $R_2$ is n-$C_{16}$-$C_{18}$ alkyl; or $CH_2CH_2OR'_2$, where $R'_2$ is as defined above;
n' is an integer 2 to 6;
and
$R_1$ and m are as defined above.

The more preferred compounds of subclass Ia are compounds of formula Ia";

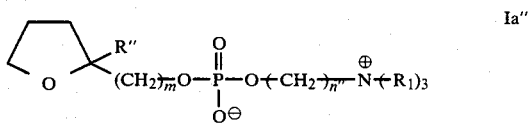

where
R" is n-$C_{16}$-$C_{18}$ alkyl or $CH_2OR'_2$, where $R'_2$ is as defined above;
n" is an integer 2 to 4;
and
$R_1$ and m are as defined above.

The even more preferred compounds of subclass Ia are compounds of formula Ia'":

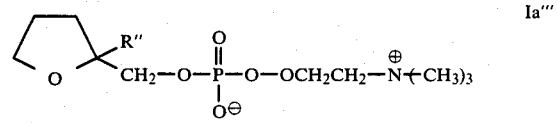

where R" is as defined above.

Also included among the compounds of formula I are the compounds of subclass Ib:

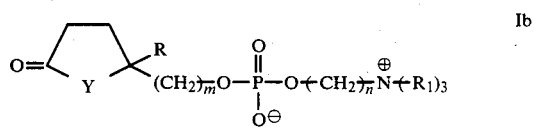

where Y is —O— or —S—; and R, $R_1$, m and n are as defined above.

The preferred compounds of subclass Ib are compounds of formula Ib':

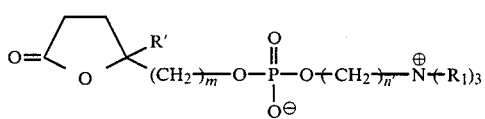

Ib' where R', $R_1$, m and n' are as defined above.

The more preferred compounds of subclass Ib are compounds of formula Ib":

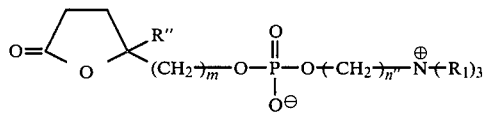

Ib"

where R", $R_1$, m and n" are as defined above.

The even more preferred compounds of subclass Ib are compounds of formula Ib'":

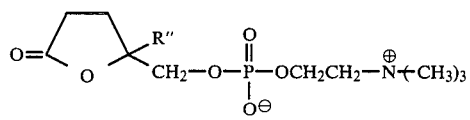

Ib'"

where R" is as defined above.

Further included among the compounds of formula I are the compounds of subclass Ic:

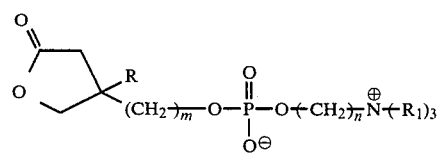

Ic where R, $R_1$, m and n are as defined above.

The preferred compounds of subclass Ic are compounds of formula Ic':

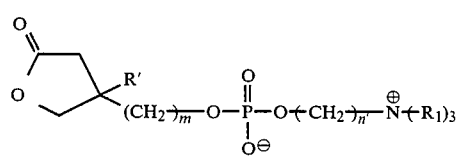

Ic' where R', $R_1$, m and n' are as defined above.

The more preferred compounds of subclass Ic are compounds of formula Ic":

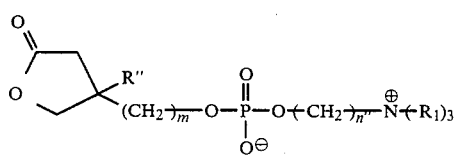

Ic"

where R", $R_1$, m and n" are as defined above.

The even more preferred compounds of subclass Ic are compounds of formula Ic'":

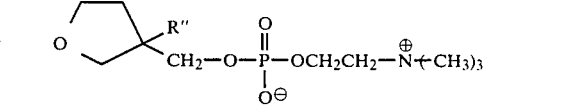

Ic'"

where R" is as defined above.

Still further included among the compounds of formula I are the compounds of subclass Id:

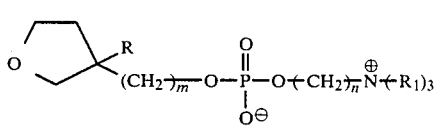

Id where R, $R_1$, m and n are as defined above.

The preferred compounds of subclass Id are compounds of formula Id':

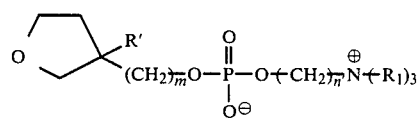

Id' where R', $R_1$, m and n' are as defined above.

The more preferred compounds of subclass Id are compounds of formula Id":

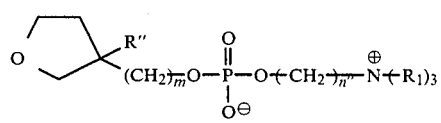

Id"

where R", $R_1$, m and n" are as defined above.

The even more preferred compounds of subclass Id are compounds of formula Id'":

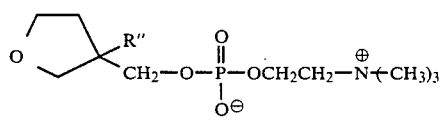

Id'"

where R" is as defined above.

The compounds of subclass Ia where Y is —O—, m is 1 and R, $R_1$ and n are as defined above may be prepared by an eight-step reaction as set forth below:

STEP 1

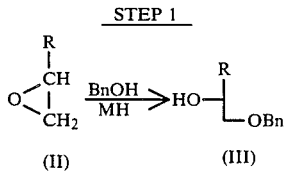

where M is an alkali metal or an alkaline earth metal cation, Bn is benzyl and R is as defined above.

STEP 2

-continued

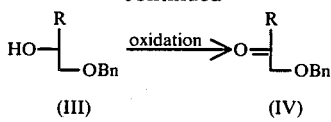

(III) (IV)

where R and Bn are as defined above.

STEP 3

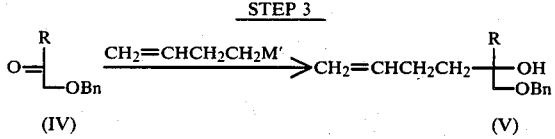

(IV) (V)

where M' is an alkali or alkaline earth metal and R and Bn are as defined above.

STEP 4

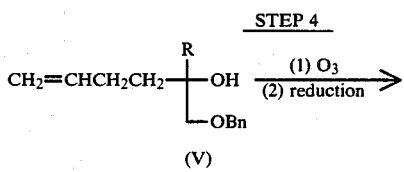

(V)

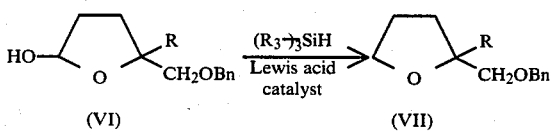

(VI)

where R and Bn are as defined above.

STEP 5

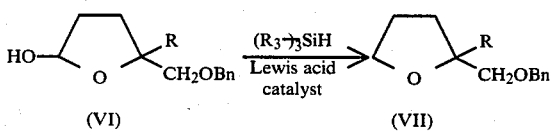

(VI) (VII)

where R and Bn are as defined above and $R_3$ is n-$C_1$-$C_4$-alkyl.

STEP 6

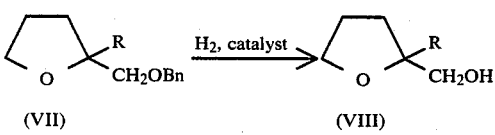

(VII) (VIII)

where R and Bn are as defined above.

STEP 7

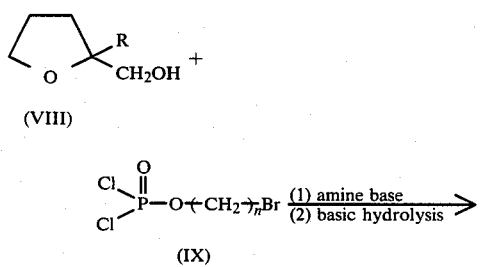

(VIII)

(IX)

-continued
STEP 7

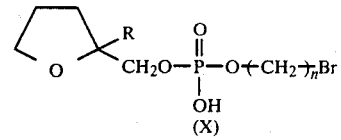

(X)

where R and n are as defined above.

STEP 8

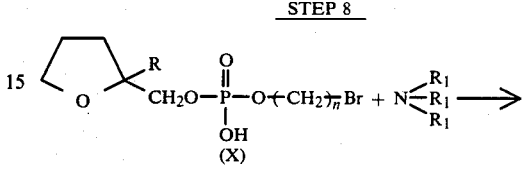

(X)

(XI)

where R, each $R_1$ and n are as defined above.

With respect to the individual steps, Step 1 concerns the reaction of an epoxide of formula II with benzyl alcohol in the presence of an alkali metal or alkaline earth metal hydride, preferably an alkali metal hydride, more preferably sodium hydride, to yield an adduct of formula III. The reaction is conveniently carried out in an inert, organic solvent, e.g., a dialkylamide such as dimethylformamide or dimethylacetamide, an aromatic hydrocarbon such as toluene, benzene or xylene, a cyclic ether such as tetrahydrofuran, or a mixture thereof. The reaction may be carried out at temperatures of from 30° to 100° C. for a period of 1 to 24 hours.

Step 2 involves the oxidation of a compound produced in Step 1, i.e., a compound of formula III, employing a chromium-based oxidant such as pyridinium chlorochromate to yield a compound of formula IV. The oxidation is carried out in an inert, organic solvent, e.g., a chlorinated hydrocarbon such as methylene chloride, at a temperature of from 20° to 40° C. for a period of between 6 and 36 hours.

Alternatively, the oxidation of a compound of formula III may be carried out employing an oxidant prepared by the action of an activating agent such as an anhydride, e.g., trifluoracetic anhydride, or an acid chloride, e.g., oxalyl chloride, on a dialkyl sulfoxide, preferably dimethyl sulfoxide, in the presence of an inert, organic solvent, e.g., a chloroinated hydrocarbon such as methylene chloride or an aromatic hydrocarbon such as toluene or xylene, at a temperature of from −78° to 25° C., preferably −78° to 0° C., followed by reaction with a $C_{1-3}$ trialkylamine, e.g., triethylamine, at a temperature of from 0° to 25° C. for a period of between 1 and 3 hours.

As to Step 3, after the preparation of an organometallic reagent by the action of an alkali or alkaline earth metal, e.g. Li or Mg, on an appropriate haloalkene such as 4-bromo-1-butene, in the presence of an aliphatic ether or a cyclic ether such as tetrahydrofuran at a temperature of from 20° to 65° C. for a period of 30 minutes to 2 hours, the organometallic compound is reacted with a compound produced in Step 2, i.e., a compound of formula IV, to yield an olefin of formula V. The reaction is conducted in the presence of the same solvent employed in preparing the organmetallic reagent or a mixture of said solvent with a compatible inert organic solvent such as pentane, hexane and the like. The reaction is carried out at a temperature of −78° to 20° C. for a period of between 30 minutes and 18 hours.

Step 4 involves subjecting a compound produced in Step 3, i.e., an olefin of formula V, to ozone in a stream of oxygen in the presence of an inert, organic solvent, e.g., a chlorinated hydrocarbon such as methylene chloride, at a temperature of from −78° to −50° C. until consumption of the olefin has been effected, after which time a reducing agent, preferably a trialkyl phosphite or dialkyl sulfide, e.g., dimethylsulfide, is added. The reduction is carried out at temperatures of from 20° to 30° C. for a period of between 1 and 24 hours to yield a compound of formula VI.

In Step 5, a compound produced in Step 4, i.e., a compound of formula VI, is reacted with a lower trialkylsilane such as triethyl silane and a Lewis acid catalyst, preferably borontrifluoride etherate, to yield a compound of formula VII. The reaction is usually conducted in the presence of a neutral solvent, e.g., a chlorinated hydrocarbon such as dichloromethane, at temperatures of from −30° to 0° C. for a period of between 1 and 4 hours.

Step 6 involves the hydrogenolysis of the benzyl ether group of a compound produced in Step 5, i.e., a compound of formula VII, by dissolving said compound in a lower alkanol, e.g., methanol, ethanol and the like, or a mixture of a lower alkanoyl and water (up to 15%), with palladium, palladium hydroxide or platinum on carbon and subjecting the resultant mixture to a pressure of between 15 and 65 lbs. of hydrogen gas at a temperature of from 20° to 50° C. for a period of between 5 and 20 hours to yield a compound of formula VIII.

Step 7 is directed to the reaction of a compound produced in Step 6, i.e., a compound of formula VIII, with a compound of formula IX, i.e., a bromoalkoxydichlorophosphate compound, e.g., 2-bromoethoxydichlorophosphate, in the presence of an amine base, such as pyridine or triethylamine. The reaction is conveniently carried out in an inert, organic solvent, e.g., an aromatic hydrocarbon such as toluene, benzene or xylene, a halogenated aliphatic hydrocarbon such as methylene chloride, chloroform or carbon tetrachloride, a halogenated aromatic hydrocarbon such as chlorobenzene, or an ether such as diethyl ether. The reaction may be carried out at temperatures of from 20° to 70° C. for a period of between 5 and 30 hours.

The second reaction in Step 7 involves subjecting the product produced in the first reaction to basic hydrolysis, e.g., by suspending the product in water. The hydrolysis is conveniently carried out at a temperature of from 20° to 100° C. for a period of from 15 minutes to about 6 hours to yield a compound of formula X.

The last step, viz., Step 8, is concerned with the reaction of a compound of formula X with a tertiary alkylamine compound to yield a compound of formula XI. The reaction is conducted in the presence of an inert, organic solvent, e.g., a lower alkanol such as methanol, ethanol and the like, an aromatic hydrocarbon such as toluene or benzene, a dialkylamide such as dimethylformamide or acetonitrile. Although the reaction temperature and time are not critical, the reaction is typically carried out at a temperature of from 50° to 70° C. for a period of time between 10 and 24 hours.

The compounds of subclass Ia where Y is —O—, m is 2 and R, R₁ and n are as defined above may be prepared according to a series of reactions commencing with the following reaction:

STEP 1-A

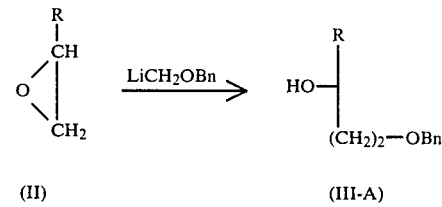

where R and Bn are as defined above. In Step 1-A, an epoxide of formula II is reacted with a benzyloxymethyl lithium compound to yield an adduct of formula III-A. The reaction is conveniently carried out in an inert, organic solvent, e.g., a lower dialkyl ether such as diethyl ether or a cyclic ether such as tetrahydrofuran at a temperature of from −100° C. to −60° C. for a period of from about 1 to about 4 hours.

Employing a compound produced in Step 1-A, i.e., a compound of formula III-A, and carrying out the reactions described above in Steps 2 through 8, results in a compound having the formula

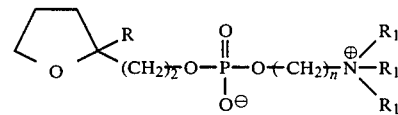

When a compound of subclass Ia is desired where Y is —O—, R is $CH_2OR_2$ or $CH_2CH_2OR_2$ and $R_1$, m and n are as defined above, it has been found more convenient to employ a three-step reaction commencing with the following reaction:

STEP A

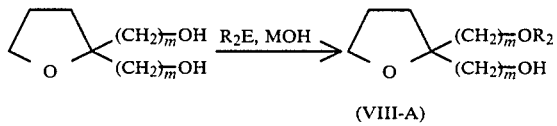

(VIII-A)

where E is chloro, bromo, iodo or tosyloxy and $R_2$, M and m are as defined above. In Step A, a diol is reacted with a halo ($C_{14-18}$) alkane, e.g., 1-bromooctadecane, or a $C_{14-18}$ para-toluenesulfonate, in the presence of an alkali metal or alkaline earth metal hydroxide, preferably an alkali metal hydroxide, to yield a compound of formula VIII-A. The reaction is conveniently carried out in the presence of an inert, organic solvent, e.g., a dialkyl amide such as dimethylformamide or dimethylacetamide, an aromatic hydrocarbon such as toluene, benzene or xylene, or a mixture of a dialkylamide, and an aromatic hydrocarbon. Alternatively, the inert, organic solvent employed may be dimethylsulfoxide, a cyclic ether such as tetrahydrofuran, or a mixture thereof. The reaction may be carried out at temperatures of from 15° to 50° C. for a period of between 1 and 6 hours.

Employing a compound produced in Step A, i.e., a compound of formula VIII-A, and carrying out the reactions described above in steps 7 and 8, results in a compound having the formula

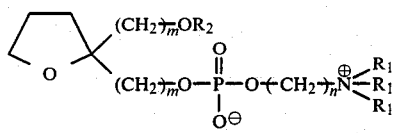

The compounds of subclass Ia where Y is —S— and R, R₁, m and n are as defined above may be prepared essentially as described above in Steps 5 through 8 with the exception that, in Step 5, a compound of the formula

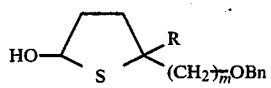

is used in place of a compound of formula VI which results, after carrying out Steps 6 through 8, in a compound having the formula

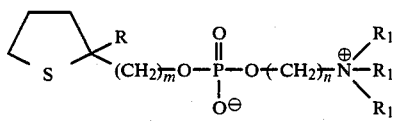

More conveniently, it has been discovered that the compounds of subclass Ia where n is 2, e.g., a compound of formula XI where n is 2, may be prepared from a compound of formula VIII by a two-step reaction as set forth below:

STEP 7A

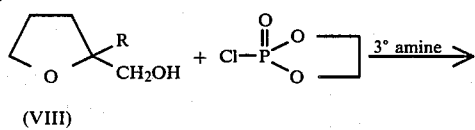

(VIII)

(XII)

where R is as defined above.

STEP 8A

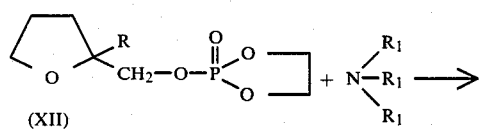

(XII)

-continued
STEP 8A

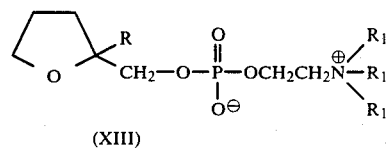

(XIII)

where R and each R₁ are as defined above.

In Step 7A, a compound of formula VIII, after dissolution in an inert, organic solvent, e.g., a halogenated hydrocarbon such as methylene chloride, chloroform and the like, or an aromatic hydrocarbon such as benzene, toluene and the like, is reacted with 2-chloro-2-oxo-1,3,2-dioxaphospholane in the presence of a tertiary amine compound, e.g., a C₁₋₄-trialkylamine such as triethylamine, and optionally a catalyst, e.g., a catalytic amount of 4-dimethylaminopyridine, to yield a compound of formula XII. The reaction is typically carried out at a temperature of from about 20° to 40° C. for a period of between 1 and 36 hours.

Step 8A involves the reaction of a compound produced in Step 7A, i.e., a compound of formula XII with a tertiary alkyl amine compound to yield a compound of formula XIII. The reaction is conducted in essentially the same manner as that described above with regard to Step 8.

The compounds of subclass Ib where Y is —O— and R, R₁, m and n are as defined above may be prepared essentially as described below:

REACTION A

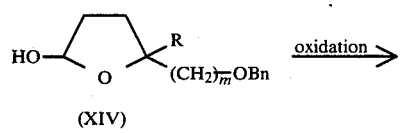

(XIV)

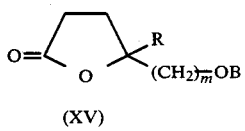

(XV)

where R, m and Bn are as defined above.

REACTION B

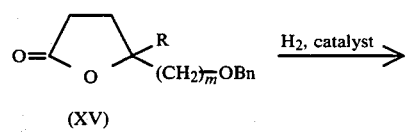

(XV)

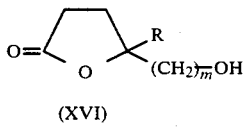

(XVI)

where R, m and Bn are as defined above.

REACTION C

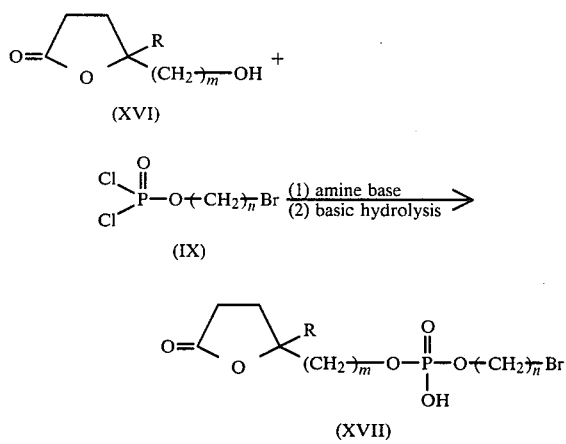

where R, m and n are as defined above.

REACTION D

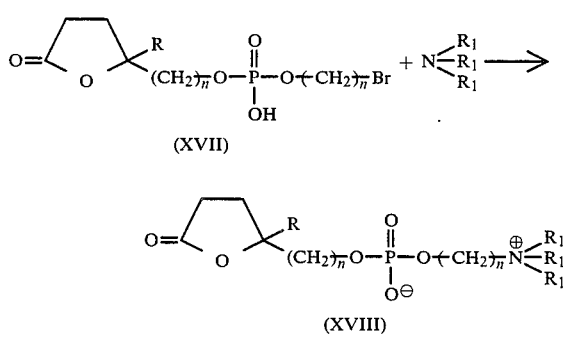

where R, each $R_1$, m and n are as defined above.

In considering the reactions individually, Reaction A concerns the oxidation of a compound of formula XIV to yield a compound of formula XV. The oxidation is carried out according to either of the procedures set forth in Step 2 above with regard to the description for preparing the compounds of subclass Ia.

Reaction B involves the hydrogenolysis of the benzyl ether group of a compound produced in Reaction A, i.e., a compound of formula XV, to yield a compound of formula XVI. The hydrogenolysis is conveniently carried out in accordance with the procedure set forth in Step 6 above with regard to the description for preparing the compounds of subclass Ia.

As to Reaction C and Reaction D for preparing a compound of formula XVII and XVIII, respectively, they are conducted in an analogous manner to that set forth above in Steps 7 and 8 regarding the description for preparing the compounds of subclass Ia.

The compounds of subclass Ib where Y is —S— and R, $R_1$, m and n are as defined above may be prepared essentially as described above in Reactions A through D with the exception that, in Reaction A, a compound of the formula

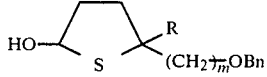

is used in place of a compound of formula XIV and the oxidation is carried out employing air or oxygen with platinum black suspended in an inert, organic solvent, e.g., a cyclic ether such as dioxane. As to reaction temperatures and times, the oxidation is carried out at a temperature of from 20° to 70° C. for a period of between 24 and 72 hours to yield a compound of the formula

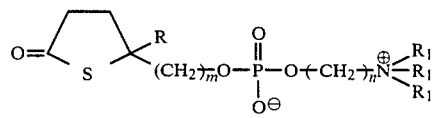

Employing the above compound, and carrying out the reactions described above in Reactions B and D results in a compound having the formula

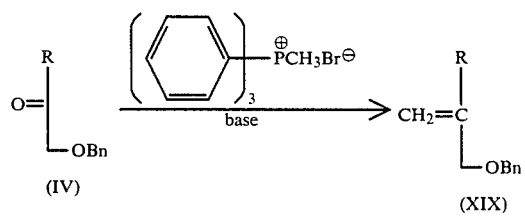

Moreover, and as was the case regarding the compounds of subclass Ia, the compounds of subclass Ib where n is 2, e.g., a compound of formula XVIII where n is 2, may be prepared essentially as described above in Steps 7A and 8A employing a compound of the formula XVI as the starting material.

The compounds of subclass Ic where m is 1 and R, $R_1$ and n are as defined above may be prepared essentially as depicted below employing a compound of formula IV as the starting material:

REACTION AA

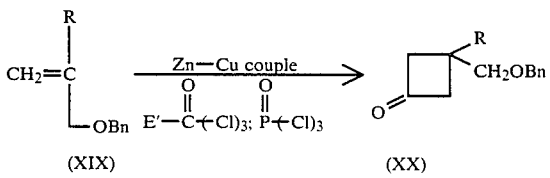

where R and Bn are as defined above.

REACTION BB

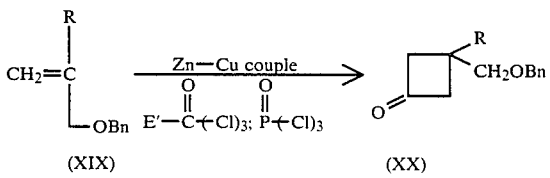

where E' is chloride or bromide, and R and Bn are as defined above.

REACTION CC

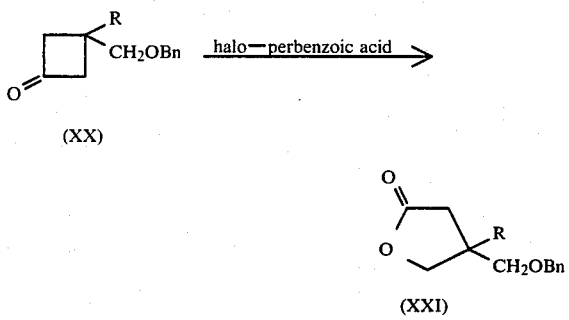

where R and Bn are as defined above.

REACTION DD

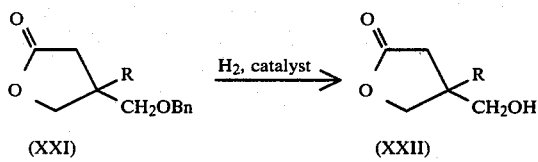

where R and Bn are as defined above.

REACTION EE

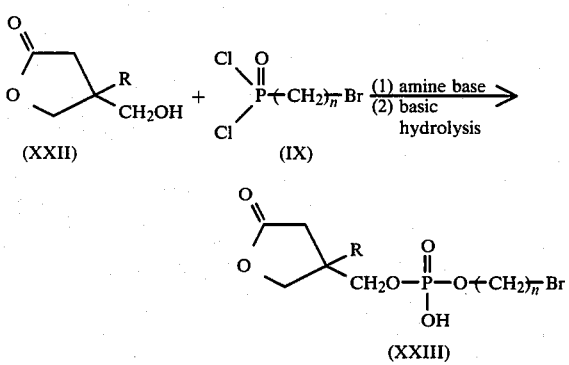

where R and n are as defined above.

REACTION FF

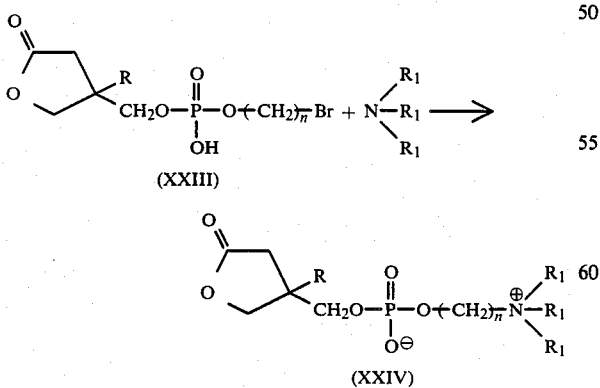

where R, R$_1$ and n are as defined above.

As to the individual reactions, Reaction AA involves the reaction of a compound of formula IV with methyl triphenylphosphonium bromide in the presence of a base such as an alkali metal or alkaline earth metal hydride, preferably an alkali metal hydride, or potassium bistrimethylsilylamide to yield an olefin of formula XIX. The reaction is conveniently carried out in an inert, organic solvent, e.g., a cyclic ether such as tetrahydrofuran and, optionally, an activating solvent such as hexamethylphosphorous triamide, at a temperature of from −70° to −20° C. for a period of 1 to 4 hours.

Reaction BB concerns ring formation whereby an olefin compound of formula XIX, after first being subjected to a zinc-copper couple, is reacted with trichloroacetylchloride or bromide, preferably trichloroacetylchloride, and phosphorus oxychloride to yield a cyclobutanone compound of formula XX. The ring-forming reaction is conducted in the presence of an inert, organic solvent, e.g., a dialkyl ether such as diethylether or methyl-t-butyl ether, or a cyclic ether such as tetrahydrofuran. As to reaction temperatures and times, the reaction is carried out at a temperature of from 20° to 40° C. for a period of between 24 and 72 hours.

As to Reaction CC, it is directed to a ring enlargement of a compound produced in Reaction BB, i.e., a cyclobutanone compound of formula XX, whereby said compound is reacted with a halo-perbenzoic acid, preferably m-chloro perbenzoic acid, to yield a furanone compound of formula XXI. The ring-enlarging reaction is typically carried out in an inert, organic solvent, e.g., a chlorinated hydrocarbon such as methylene chloride, chloroform and the like, at a temperature of from 40° to 60° C. for a period of between 6 and 15 hours.

Reaction DD involves the hydrogenolysis of the benzyl ether group of a compound produced in Reaction CC, i.e., a compound of formula XXI, to yield a compound of formula XXII. The hydrogenolysis is conveniently carried out in accordance with the procedure set forth in step 6 above with regard to the description for preparing the compounds of subclass Ia.

As to Reaction EE and Reaction FF for preparing a compound of formula XXIII and XXIV, respectively, they are conducted in an analogous manner to that set forth above in Steps 7 and 8 regarding the description for preparing the compounds of subclass Ia.

The compounds of subclass Ic where m is 2 and R, R$_1$ and n are as defined above may be prepared according to a series of reactions commencing with Step 1-A above and, employing a compound produced in Step 1-A, i.e., a compound of formula III-A, and carrying out the reactions described above in Step 2 and Reactions AA through FF, results in a compound having the formula

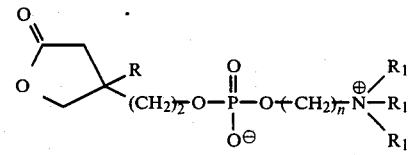

Moreover, and as was the case regarding the compounds of subclass Ia, the compounds of subclass Ic where n is 2, e.g., a compound of formula XXIV where n is 2, may be prepared essentially as described above in Steps 7A and 8A employing a compound of the formula XXII as the starting material.

The compounds of subclass Id where m is 1 and R, $R_1$ and n are as defined above may be prepared in a series of steps commencing with the following two-part reaction employing a compound of formula XXI as a starting material:

STEP AA

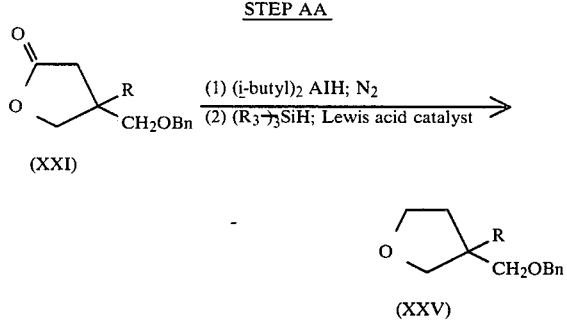

(XXI) → (XXV)

where R, $R_3$ and Bn are as defined above. In the first part, a furanone compound of formula XXI is reacted with di-isobutyl aluminum hydride in a nitrogen atmosphere at a temperature of from −80° to −50° C. for a period of between 2 and 5 hours. The resultant product is then reacted, in a second part, with a lower trialkylsilane, preferably triethysilane, and a Lewis acid catalyst, preferably borontrifluoride etherate, to yield a tetrahydrofuran compound of formula XXV.

Employing a compound produced in Step AA, i.e., a compound of formula XXV, and carrying out the reactions described above in Reactions DD through FF, results in a compound having the formula

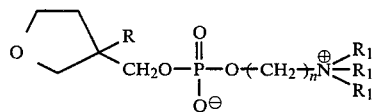

The compounds of subclass Id where m is 2 and R, $R_1$ and n are as defined above may be prepared according to a series of reactions commencing with Step 1-A above and, employing a compound produced in Step 1-A, i.e., a compound of formula III-A, and carrying out the reactions described above in Step 2, Reactions AA through CC, Step AA and Reactions DD through FF results in a compound having the formula

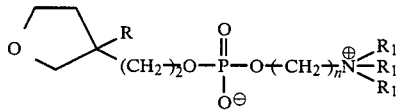

Moreover, and as was the case regarding the compounds of subclass Ia, the compounds of subclass Id where n is 2 may be prepared essentially as described above in Steps 7A and 8A employing a compound of the formula

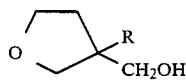

as the starting material.

As to any of the particular starting materials set forth above, e.g., compounds of formulae II, IX, etc., they are either known and obtained by methods described in the literature, or where not known, may be obtained by methods analogous to those described in the literature.

The product of each reaction may, if desired, be purified by conventional techniques such as recrystallization (if a solid), column chromatography, preparative thin layer chromatography, gas chromatography (if sufficiently volatile), or fractional distillation under high vacuum (if sufficiently volatile). Often, however, the crude product of one reaction may be employed in the following reaction without purification.

As is evident to those skilled in the art, all of the compounds of formula I can exist as stereoisomers and such isomers and their enantiomers are contemplated as being including within the scope of this invention.

As indicated above, all of the compounds of formula I are anti-tumor agents and are, therefore, useful in inhibiting the growth of various lymphomas, sarcomas, myelomas and leukemia cell lines. The anti-tumor activity of the compounds of formula I may be demonstrated employing the Tumor Cell Cytotoxicity test (TCC test) as follows:

In flat bottom microtiter plates (Nunc Roskilde, Denmark) were placed Abelson 8.1 lymphoma, YAC, L1210, P815, Meth A fibrosarcoma or fresh human neuroblastoma tumor cells in DMEM+10% fetal calf serum and the tumor cell-containing plates were incubated with 1,3 and 5 μg of the test compound for a period of 6 to 72 hours. The number of tumor cells present in the Abelson 8.1, YAC, L1210 and P815 assays was determined by measuring the alkaline phosphatase as follows:

The tumor cell plates were centrifuged (500×g) for ten minutes and the supernatant flicked off. Without further washing, 100 μl of buffer containing 20 μl of diethanolamine, 2 μM of $MgCl_2.6H_2O$, 2.5 μM of p-nitrophenylphosphate and 10 mg Triton X-100 were added. The samples were incubated for 60 minutes at room temperature and the enzymatic reaction was terminated by the addition of 100 μl of 0.5N NaOH. The absorbance was then measured at 405 nm using a Titertek Multiskan apparatus.

The number of tumor cells present in the Meth A fibrosarcoma and human neuroblastoma assays was measured by $^3$H-thymidine uptake as follows:

After 72 hours, the cells are thoroughly washed, and each well treated with ca. 0.1 μC $^3$H-thymidine. After 4–6 hours, the cells are collected using a commercial cell harvester, and the radioactivity in the filtrate is measured in a scintillation counter.

At a concentration of 5 μg and an incubation period of 72 hours, the following results were obtained:

| | % Inhibition | | | | | |
|---|---|---|---|---|---|---|
| | Abel. | YAC | L1210 | P815 | Meth A | neuro. |
| Ex. 2 | 97 | 71 | 69 | 84 | 98 | 59 |
| Ex. 5 | 98 | 96 | — | — | — | — |
| Ex. 6 | 50–70 | | | | | |
| Ex. 7 | 70–90 | | | | | |

The anti-tumor activity of the compounds of formula I may also be demonstrated employing the Influence on Cytotoxicity of ET-18-OCH$_3$ test as follows:

Bone marrow cell macrophages ($10^5$/well) obtained from [BALB/CX57/BL$_6$]Fl mice were incubated with 10 μg of 1-octadecyl-2-methoxy-3-phosphoryl choline (ET-18-OCH$_3$) for 24 hours in flat bottom microtiter plates (Nunc Roskilde, Denmark), after which time they are centrifuged and washed once. Abelson 8.1 tumor cells in DMEM+10% fetal calf serum and 1,3 and 5 μg of the test compound were then added to the plates. With the cytotoxicity of ET-18-OCH$_3$ (10 μg) alone set at 100%, the inhibition or enhancement of the cytotoxic effect, as measured by an alkaline phosphatase assay, was determined and values recorded after 72 hours for 1, 3 and 5 ηg of the test substance. At a concentration of 5 μg, the following results were obtained:

|  | % Enhancement |
|---|---|
| compound of Ex. 2 | 99.5 |
| compound of Ex. 5 | >90 |
| compound of Ex. 6 | 90 |
| compound of Ex. 7 | 90 |

The usefulness of the compounds of formula I in treating tumors may additionally be demonstrated employing the following procedure:

Meth A fibrosarcoma cells were induced in BALB/C mice by administering methylcholanthrene according to the procedure of Old, et al. (L. J. Old, E. A. Boyse, D. A. Clarke, and E. Carswell, Ann. N.Y. Acad. Sci., 101, 80 (1962). These tumor cells were harvested from the peritoneal cavity 10 to 12 days after administration of methylcholanthrene. Ten CBF$_1$ mice of 10–12 week age were each implanted with 7.3×10$^6$ Meth A sarcoma cells to serve as control. A second group of ten CBF$_1$ mice were each implanted with 7.3×10$^6$ Meth A sarcoma cells and on day one after implant each mouse was treated p.o. with 5–50 μg of the test compound per day for a total of twenty or twenty-seven days. Tumor growth and survivors were assayed on days 7, 14, 21 and 28 after tumor implantation. Under these conditions, none of the control group animals survived, whereas 5 out of 10 animals which were administered 50 μg of the compound of Example 2 for 28 days survived and 8 out of 10 animals which were administered 50 μg of the compound of Example 5 for 28 days survived. Moreover, most of the survivors showed no evidence of any tumors.

The precise dosage of the compounds of formula I to be employed for inhibiting tumors depends upon several factors including the host, the nature and the severity of the condition being treated, the mode of administration and the particular compound employed. However, in general, satisfactory inhibition of tumors is achieved when a compound of formula I is administered orally or intravenously at a daily dosage of 1–100, preferably 5–35 mg/kg body weight or, for most larger primates, a daily dosage of 500–2000 mg, preferably 1000–1500 mg. A typical oral dosage is 400 mg, two to three times a day, or 20 mg/kg intravenously over a 24 hour period.

Usually, a small dosage is administered initially and the dosage is gradually increased until the optimal dosage for the host under treatment is determined. For parenteral administration, e.g., i.v. or i.p., a dosage somewhat lower than would be used for oral administration of the same compound to the same host having the same condition is usually employed. The upper limit of dosage is that imposed by side effects, and can be determined by trial for the host being treated, including humans.

A typical dosage unit for oral administration may contain 300 to 600 mg of a compound of formula I. Preferred oral dosage units contain 300 to 500 mg, especially 350 to 450 mg of a compound of formula I.

The compounds of formula I may be combined with one or more pharmaceutically acceptable carriers and, optionally, one or more other conventional pharmaceutical adjuvants and administered orally in the form of tablets, dispersible powders, granules, capsules, elixirs, suspensions and the like or parenterally in the form of sterile injectable solutions or suspensions. The compositions may be prepared by conventional means.

The compounds of formula I may be formulated into such pharmaceutical compositions containing an amount of the active substance that is effective for inhibiting tumors, such compositions in unit dosage form and such compositions comprising a solid pharmaceutically acceptable carrier.

Tablets and capsules containing the ingredients indicated below may be prepared by conventional techniques and are useful as anti-tumor agents. The tablet may be administered two to four times a day whereas the capsule is suitably administered three times a day.

| Ingredients | Weight (mg) tablet | capsule |
|---|---|---|
| compound of formula I, e.g. the compound of Example 2 | 400 | 400 |
| tragacanth | 10 | — |
| lactose (spray-dried) | 197.5 | 250 |
| corn starch | 25 | — |
| talcum | 15 | — |
| magnesium stearate | 2.5 | — |
| Total | 650.0 | 650 |

The preferred pharmaceutical compositions from the standpoint of preparation and ease of administration are solid compositions, particularly liquid or hard-filled capsules and tablets containing from about 350 to 450 milligrams of the active ingredient.

The following examples show representative compounds encompassed by this invention and their synthesis. However, it should be clearly understood that they are for purposes of illustration only.

EXAMPLE 1

2-[hydroxy(tetrahydro)-2-(octadecyloxymethyl-5-oxo-2-furanyl)methoxyphosphinyloxy]N,N,N-trimethylethanaminium hydroxide, inner salt-4-oxide

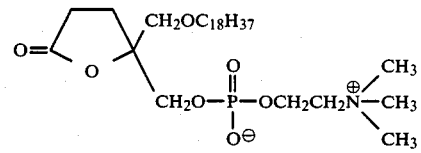

(A) Preparation Of 1-0-octadecyl-3-0-benzylglycerol

To 12.0 g of 60% sodium hydride in mineral oil (30 mmol; washed free of oil by the use of petroleum ether) was added 32.4 g (300 mmol) of benzyl alcohol in 200 ml of dry dimethylformamide. The suspension was heated under a flow of nitrogen to 80° C. and maintained at this temperature for 45 minutes, after which time 63.2 g (0.19 mol) of an epoxide (prepared by the peracid oxidation of allyloctadecylether) in 100 ml of dimethyl formamide was added and the temperature maintained at 80° C. for 15 hours. The solvent was then removed in vacuo and the residue chromatographed on silica gel employing a mixture of petroleum ether and diethyl ether in a ratio of 3:2 as the eluent to yield a low-melting waxy solid.

(b) Preparation of 1-0-octadecyl-3-0-benzyldihydroxyacetone

To a complex prepared at −60° C. from the addition of 10.4 ml of dry dimethyl sulfoxide to 8.9 g (70 mmol) of oxalyl chloride in 150 ml of methylene chloride, was added, dropwise, 27.0 g (62.2 mmol) of the compound prepared in (a) above. After stirring the mixture under a nitrogen atmosphere for 1 hour, 50 ml of triethylamine in 50 ml of methylene chloride was added and the resultant mixture was allowed to warm to 0° C. over a period of 30 minutes, after which time it was quenched with 75 ml of water. After the mixture was allowed to warm to room temperature, the organic layer was separated, washed with a saturated sodium chloride solution, dried over magnesium sulfate and concentrated in vacuo to afford an oil which solidified on standing. Flash chromatography on silica gel employing a mixture of petroleum ether and diethyl ether in a ratio of 7:3 as the eluent yielded a white solid.

(c) Preparation of 2-benzyloxymethyl-2-hydroxy-1-octadecyloxyhex-5-ene 1.12 g (8 mmol) of 4-bromo-1-butene in 15 ml of dry ether was reacted with 200 mg of magnesium turnings at reflux under a nitrogen atmosphere for 1 hour. The resulting Grignard reagent was cooled to −60° C. and then treated with 2.16 g (5 mmol) of the compound prepared in (b) above in 30 ml of ether. After 1 hour at −60° C., the mixture was warmed overnight to room temperature and then quenched with a saturated aqueous ammonium acetate solution and partitioned. The organic layer was then washed twice with ammonium acetate, washed with a saturated sodium chloride solution and dried over magnesium sulfate, after which time the solvent was removed under reduced pressure. Purification of the crude product was effected on silica gel employing a mixture of petroleum ether and diethyl ether as the eluent to yield a colorless oil.

(d) Preparation of 5-benzyloxymethyl-2-hydroxy-5-octadecycloxymethyl-tetrahydrofuran 6.0 g (12.3 mmol) of the compound prepared in (c) above in 100 ml of methylene chloride was treated with ozone at −60° C. After consumption of the olefin, 25 ml of dimethylsulfide was added and the mixture allowed to warm to room temperature. The solvent was removed in vacuo and the crude product was purified on silica gel employing a mixture of petroleum ether and diethylether in a ratio of 7:3 as the eluent to yield a colorless oil.

(e) Preparation of 5-benzyloxymethyl-5-octadecyloxymethyl-4,5-dihydro-2(3H)furanone To a solution of 1.6 g (7.4 mmol) of pyridinium chlorochromate in 25 ml of methylene chloride under a nitrogen atmosphere, was added 13.2 g (6.5 mmol) of the compound prepared in (d) above in 25 ml of methylene chloride. After 18 hours at 25° C., the solution was diluted with 150 ml of ether, filtered through silica gel and the filtrate evaporated to afford an oil. The oil was then flash chromatographed on silica gel employing a mixture of petroleum ether and diethyl ether in a ratio of 7:3 as the eluent to yield a colorless oil.

(f) Preparation of 5-hydroxymethyl-5-octadecyloxymethyl-4,5-dihydro-2(3H)furanone A mixture containing 10.7 g (21.83 mmol) of the compund prepared in (e) above, 300 ml of a mixture of ethyl alcohol and water in a ratio of 9:1 and 1.5 g of 5% palladium on carbon (50% water content) was placed in a pressure bottle and hydrogenated at b 40° C. under a pressure of 50 lbs. of hydrogen until uptake was complete. The catalyst was then filtered off and the filtrate concentrated in vacuo. The residue was crystallized from methanol to yield a solid.

Preparation of the title compound

To 860 mg (2.16 mmol) of the compound prepared in (f) above, 29 mg (0.24 mmol) of 4-dimethylaminopyridine and 0.42 ml (3 mmol) of triethylamine in 10 ml of benzene, was added 455 mg (3.2 mmol) of 2-chloro-2-oxo-1,3,2-dioxaphospholane. The resultant mixture was allowed to stir at room temperature for 18 hours, after which time it was filtered and the filtrate was evaporated to dryness. The residue was taken up with 10 ml of dry acetonitrile, cooled to allow introduction of excess condensed trimethylamine, and then heated in a sealed tube under pressure for 20 hours at 70° C. The reaction mixture was then cooled to room temperature, diluted with an equal volume of acetonitrile and filtered to afford a white solid which was recrystallized from a mixture of methylene chloride and acetone to yield a solid, m.p. 215°–220° C. (dec.).

EXAMPLE 2

2-[hydroxy(tetrahydro)-2-(octadecyl-5-oxo-2-furanyl)-methoxyphosphinyloxy]-N,N,N-trimethyl-ethanaminium hydroxide, inner salt-4-oxide

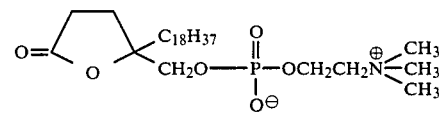

(a) Preparation of 1-benzyloxy-2-eicosanol

Following essentially the procedure of Example 1(a), and using in place of allyloctadecylether, an approximately equivalent amount of 1-eicosene, a wax-like solid was obtained.

(b) Preparation of 1-benzyloxy-2-eicosanone

Following essentially the procedure of Example 1(b), and using in place of the compound prepared in 1(a), an equivalent amount of the compound prepared in 2(a) above, a solid was obtained.

(c) Preparation of 5-benzyloxymethyl-5-hydroxy-1-tricosene

Following essentially the procedure of Example 1(c), and using in place of the compound prepared in 1(b), an equivalent amount of the compound prepared in 2(b), above, a low melting solid was obtained.

(d) Preparation of
5-benzyloxymethyl-2-hydroxy-5-octadecyl
tetrahydrofuran

Following essentially the procedure of Example 1(d), and using in place of the compound prepared in 1(c), an equivalent amount of the compound prepared in 2(c) above, an oil was obtained.

(e) Preparation of
5-benzyloxymethyl-5-octadecyl-4,5-dihydro-2(3H)furanone

Following essentially the procedure of Example 1(e), and using in place of the compound prepared in 1(d), an equivalent amount of the compound prepared in 2(d) above, a colorless oil was obtained.

(f) Preparation of
5-hydroxymethyl-5-octadecyl-4,5-dihydro-2(3H)furanone

Following essentially the procedure of Example 1(f), and using in place of the compound prepared in 1(e), an equivalent amount of the compound prepared in 2(e) above, a solid was obtained.

Preparation of the title compound

Following essentially the last step of the procedure in preparing the compound of Example 1, and using in place of the compound prepared in 1(f), an equivalent amount of the compound prepared in 2(f) above, a white solid was obtained, m.p. 235°–240° C.

(d) Preparation of
5-benzyloxymethyl-2-hydroxy-5-(2-octadecyloxyethyl)-tetrahydrofuran Following essentially the procedure of Example 1(d), and using in place of the compound prepared in 1(c), an approximately equivalent amount of the compound prepared in 3(c) above, a colorless oil was obtained.

(e) Preparation of
5-benzyloxymethyl-5-(2-octadecyloxyethyl)-4,5-dihydro-2(3H)-furanone Following essentially the procedure of Example 1(e), and using in place of the compound prepared in 1(d), an approximately equivalent amount of the compound prepared in 3(d) above, a colorless oil was obtained.

(f) Preparation of
5-hydroxymethyl-5-(2-octadecyloxyethyl)-4,5-dihydro-2(3H)furanone Following essentially the procedure of Example 1(f), and using in place of the compound prepared in 1(e), an approximately equivalent amount of the compound prepared in 3(e), above, a solid was obtained.

Preparation of the title compound

Following essentially the last step of the procedure in preparing Example 1, and using in place of the compound prepared in 1(f), an approximately equivalent amount of the compound prepared in 3(f) above, a foamy solid was obtained, m.p. 107° C. (dec.)

EXAMPLE 3

2-[hydroxy-[tetrahydro-2-(2-octadecyloxyethyl)-5-oxo-2-furanyl]-methoxyphosphinyloxy]-N,N,N-trimethyl ethanaminimum hydroxide, inner salt-4-oxide

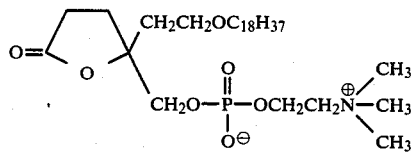

EXAMPLE 4

2-[hydroxy-2-[tetrahydro-2-(octadecyloxymethyl)-5-oxo-2-furanyl]-ethoxyphosphinyloxy]-N,N,N-trimethyl ethanaminimum hydroxide, inner salt-4-oxide

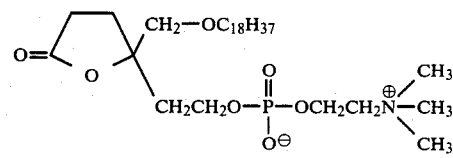

(a) Preparation of
1-benzyloxy-4-octadecyloxy-butane-2-ol

Following essentially the procedure of Example 1(a), and using instead of allyloctadecylether, an approximately equivalent amount of octadecyl-3-butenyl ether, there was obtained a wax-like solid.

(b) Preparation of
1-benzyloxy-4-octadecyloxy-2-butanone

Following essentially the procedure of Example 1(b), and using in place of the compound prepared in 1(a), an approximately equivalent amount of the compound prepared in 3(a), above, a solid was obtained.

(c) Preparation Of
3-benzyloxymethyl-3-hydroxy-1-octadecyloxy-hept-6-ene

Following essentially the procedure of Example 1(c), and using in place of the compound prepared in 1(b), an approximately equivalent amount of the compound prepared in 3(b) above, there was obtained a low melting solid.

(a) Preparation of
1-benzyloxy-4-octadecyloxy-butane-3-ol

Following essentially the procedure of Example 1(a), and using in place of allyloctadecylether, an approximately equivalent amount of benzyl-3-butenyl ether, and in place of benzyl alcohol, an approximately equivalent amount of 1-octadecanol, a wax-like solid was obtained.

(b) Preparation of
1-benzyloxy-4-octadecyloxy-3-butanone

Following essentially the procedure of Example 1(b), and using in place of the compound prepared in 1(a), an approximately equivalent amount of the compound prepared in 4(a) above, a solid was obtained.

(c) Preparation of
2-(2-benzyloxyethyl)-2-hydroxy-1-octadecyloxyhex-5-ene

Following essentially the procedure of Example 1(c), and using in place of the compound prepared in 1(b), an approximately equivalent amount of the compound prepared in 4(b) above, a low-melting solid was obtained.

(d) Preparation of 5-(2-benzyloxyethyl)-2-hydroxy-5-octadecyloxymethyl tetrahydrofuran Following essentially the procedure of Example 1(d), and using in place of the compound prepared in 1(c), an approximately equivalent amount of the compound prepared in 4(c) above, an oil was obtained.

(e) Preparation of 5-(2-benzyloxyethyl)-5-octadecyloxymethyl-4,5-dihydro-2(3H)furanone Following essentially the procedure of Example 1(e), and using in place of the compound prepared in 1(d), an approximately equivalent amount of the compound prepared in 4(d) above, a colorless oil, partially solidifying at room temperature, was obtained.

Preparation of 5-(2-hydroxyethyl)-5-octadecyloxymethyl-4,5-dihydro-2(3H) furanone Following essentially the procedure of Example 1(f), and using in place of the compound prepared in 1(e), an approximately equivalent amount of the compound prepared in 4(e) above, a solid was obtained.

Preparation of the title compound

Following essentially the last step of the procedure in preparing the compound of Example 1, and using in place of the compound prepared in 1(f), an approximately equivalent amount of the compound prepared in 4(f) above, a foamy solid was obtained, m.p. 145° C. (dec.)

EXAMPLE 5

2-[(2-octadecyloxymethyltetrahydro-2-furanylmethoxy)-hydroxyphoshphinyloxyl]-N,N,N-trimethylethanaminium hydroxide inner salt-4-oxide

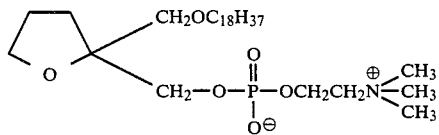

(a) Preparation of tetrahydro-2-octadecyloxymethyl-2-furanmethanol

To a mixture of 2.64 g (0.002 mol) of 2,2-bis(hydroxymethyl)-tetrahydrofuran and 2.2 g (0.0066 mol) of bromooctadecane in 8 ml of 1:1 mixture of dimethylsulfoxide and tetrahydrofuran was added 1.84 g (0.0264 mol) of finely powdered potassium hydroxide. The resultant mixture was then stirred at room temperature for 2 hours, after which time it was poured onto 100 ml of water, diluted with 20 ml of an aqueous saturated sodium chloride solution and extracted with ether. The ether extract was then washed with an aqueous saturated sodium chloride solution, dried over anhydrous sodium sulfate and the ether was removed under reduced pressure. The crude product was then purified by column chromatography on silica gel employing a mixture of methyl-t-butyl ether and hexane (3:1 ratio) as the eluent to yield the desired compound as a wax.

Preparation of the title compound

Following essentially the last step of the procedure in preparing the compound of Example 1, and using in place of the compound prepared in 1(f), an approximately equivalent amount of the compound prepared in (a) above, a white solid was obtained, m.p. 232°–235° C. (dec.).

EXAMPLE 6

2-[hydroxy(tetrahydro)-3-(octadecyl-5-oxo-3-furanyl)-methoxyphosphinyloxy]-N,N,N-trimethyl ethanaminium hydroxide, inner salt-4-oxide

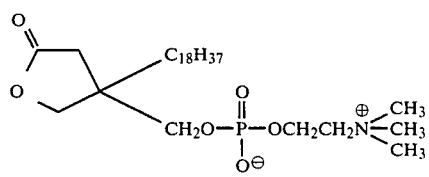

(a) Preparation of 2-benzyloxymethyl-1-eicosene

To a stirred suspension of 5.0 g of methyl triphenylphosphonium bromide in 50 ml of anhydrous tetrahydrofuran and 4.0 ml of hexamethylphosphorous triamide was gradually added 27 ml of 0.5M potassium bis-trimethylsilylamide. The resultant mixture was then stirred at room temperature for 30 minutes, after which time it was cooled to −60° C. (dry ice/acetone bath) and treated dropwise with a solution of 8.0 g (210 mmol) of the compound of Example 2(b) in 50 ml of anhydrous tetrahydrofuran and stirred for 1 hour at −60° C. and for 1 hour at ice bath temperature. The solids were then filtered off and the filtrate evaporated in vacuo to afford an oil. The oil was then chromatographed on silica gel employing a mixture of petroleum ether and methyl-t-butyl ether in a ratio of 9:1 as the eluent to yield a yellow oil.

(b) Preparation of 3-benzyloxymethyl-3-octadecyl cyclobutanone

A stirred mixture containing 7.18 g (18 mmol) of the compound prepared in (a) above, 75 ml of anhydrous diethyl ether and 1.4 g of zinc-copper couple was blanketed with nitrogen and treated dropwise at room temperature with a solution containing 3.63 g (20 mmol) of trichloroacetyl chloride and 3.06 g (20 mmol) of phosphorus oxychloride. After stirring the mixture at room temperature for 48 hours, the salts were filtered off and the filtrate concentrated in vacuo. The residue was then chromatographed on silica gel employing a mixture of petroleum ether and methyl-t-butyl ether in a ratio of 9:1 as the eluent to yield a yellow oil.

(c) Preparation of 4-benzyloxymethyl-4-octadecyl-4,5-dihydro-2(3H)-furanone

A stirred solution containing 2.27 g (5.1 mmol) of the compound prepared in (b) above and 2.2 g (12.75 mmol) of m-chloroperbenzoic acid in 30 ml of anhydrous methylene chloride was refluxed for 10 hours under a nitrogen atmosphere. The reaction mixture was then cooled to room temperature, washed with 10 ml of a 2M sodium bisulfite solution, washed twice with 10 ml of a 2M sodium bicarbonate solution and washed with 10 ml of brine, after which time it was dried over magnesium sulfate, filtered and evaporated to afford a colorless liquid. The liquid was then chromatographed on silica gel employing a mixture of petroleum ether and methyl-t-butyl ether in a ratio of 7:3 as the eluent to yield a colorless liquid.

(d) Preparation of 4-hydroxymethyl-4-octadecyl-4,5-dihydro-2(3H) furanone

Following essentially the procedure of Example 1(f), and using in place of the compound prepared in 1(e), an equivalent amount of the compound prepared in 6(c) above, a solid was obtained.

Preparation of the title compound

Following essentially the last step of the procedure in preparing the compound of Example 1, and using in place of the compound prepared in 1(f), an equivalent amount of the compound prepared in 6(d) above, a white solid was obtained, m.p. 251°-254° C. (dec.)

EXAMPLE 7

2-[(3-octadecyltetrahydro-3-furanylmethoxy)-hydroxy-phosphinyloxy]-N,N,N-trimethyl ethanaminium hydroxide, inner salt-4-oxide

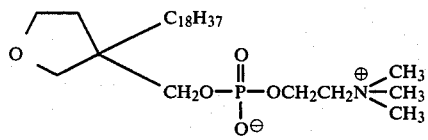

(a) Preparation of 3-benzyloxy-3-octadecyl tetrahydrofuran

A solution of 1.0 g (2.1 mmol) of the compound of Example 6(c) in 25 ml of anhydrous toluene under a nitrogen atmoshpere was cooled to −70° C. (methanol/dry ice bath) and treated dropwise, over a period of 45 minutes, with 3.2 ml of 1.0M di-isobutyl aluminum hydride. The resultant mixture was then stirred for an additional 2 hours, while the temperature was maintained at −70° C., after which time it was carefully poured onto a mixture of 1 ml of acetic acid and 80 g of ice/water. The organic layer was then separated and the aqueous layer extracted twice with 20 ml of toluene The combined toluene layers were then washed with 20 ml of a 1N sodium bicarbonate solution and washed twice with 20 ml of brine, after which time they were dried over magnesium sulfate, filtered and evaporated to an oil. The oil was then dissolved in a solution containing 0.366 g (3.15 mmol) of triethylsilane and 10 ml of dry methylene chloride, cooled to −20° C. (isopropanol/dry ice bath) and treated with 0.326 g (2.3 mmol) of boron trifluoride etherate. The resultant mixture was then stirred for 1 hour, while the temperature was maintained at −20°° C., after which time 5 ml of a 1N sodium bicarbonate solution was added and the mixture allowed to warm to room temperature. The organic layer was then separated, washed with 5 ml of brine, dried over anhydrous magnesium sulfate, filtered and concentrated in vacuo to afford an oil. The oil was then chromatographed on silica gel employing a mixture of petroleum ether and methyl-t-butyl ether in a ratio of 9:1 as the eluent to yield an oil.

(b) Preparation of 3-octadecyl-tetrahydro-2-furan methanol

Following essentially the procedure of Example 1(f), and using in place of the compound prepared in 1(e), an equivalent amount of the compound prepared in 7(a) above, a low melting solid was obtained.

Preparation of the title compound

Following essentially the last step of the procedure in preparing the compound of Example 1, and using in place of the compound prepared in 1(f), an equivalent amount of the compound prepared in 7(b) above, a white solid was obtained, m.p. 235°-241° C. (dec.)

EXAMPLE 8

2-[hydroxy(tetrahydro)-3-(octadecyloxymethyl-5-oxo-3-furanyl)methoxyphosphinyloxy]N,N,N-trimethyl ethanaminium hydroxide, inner salt-4-oxide

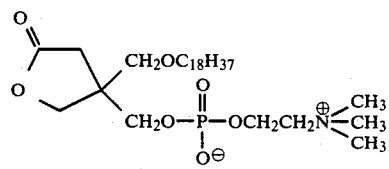

(a) Preparation of 2-benzyloxymethyl-3-octadecyloxy prop-1-ene

Following essentially the procedure of Example 6(a), and using in place of the compound prepared in 2(b), an equivalent amount of the compound prepared in 1(b), an oil was obtained.

(b) Preparation of 3-benzyloxymethyl-3-octadecyloxymethyl cyclobutanone

Following essentially the procedure of Example 6(b), and using in place of the compound prepared in 6(a), an equivalent amount of the compound prepared in 8(a) above, a yellow oil was obtained.

(c) Preparation of 4-benzyloxymethyl-4-octadecyloxymethyl-4,5-dihydro-2(3H)-furanone Following essentially the procedure of Example 6(c), and using in place of the compound prepared in 6(b), an equivalent amount of the compound prepared in 8(b) above, a colorless oil was obtained.

(d) Preparation of 4-hydroxyethyl-4-octadecyloxymethyl-4,5-dihydro-2(3H)furanone Following essentially the procedure of Example 1(f), and using in place of the compound prepared in 1(e), an equivalent amount of the compound prepared in 8(c) above, a colorless oil was obtained.

Preparation of the title compound

Following essentially the last step of the procedure in preparing the compound of Example 1, and using in place of the compound prepared in 1(f), an equivalent amount of the compound prepared in 8(d) above, a white solid was obtained, m.p. 220°-225° C. (dec.)

What is claimed is:
1. A compound of formula I:

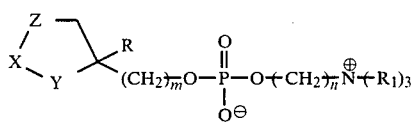

where
- R is n-$C_{14}$-$C_{18}$ alkyl; $CH_2OR_2$, where $R_2$ is n-$C_{14}$-$C_{18}$ alkyl; or $CH_2CH_2OR_2$, where $R_2$ is as defined above;
- $R_1$ is n-$C_1$-$C_3$ alkyl;
- X is —$CH_2$—, C=O or —O—;
- Y is —$CH_2$—, —O— or —S—;
- Z is —$CH_2$— or C=O;
- m is an integer 1 or 2;

and
- n is an integer 2 to 8; with the provisos that: (1) when X is —O—, Y is —$CH_2$—; and (2) when Y is —O— or —S— and X is —$CH_2$— or C=O, Z is —$CH_2$—.

2. A compound according to claim 1 of formula Ia:

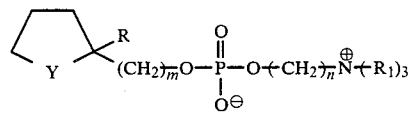

where Y is —O— or —S—; and R, $R_1$, m and n are as defined in claim 1.

3. A compound according to claim 2 of formula Ia':

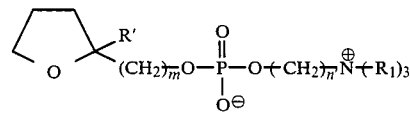

where
- R' is n-$C_{16}$-$C_{18}$ alkyl; $CH_2OR'_2$, where $R'_2$ is n-$C_{16}$-$C_{18}$ alkyl; or $CH_2CH_2OR'_2$, where $R'_2$ is as defined above;
- n' is an integer 2 to 6;

and
$R_1$ and m are as defined in claim 2.

4. A compound according to claim 3 of formula Ia":

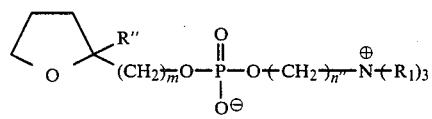

where
- R" is n-$C_{16}$-$C_{18}$ alkyl or $CH_2OR'_2$, where $R'_2$ is as defined in claim 3;
- n" is an integer 2 to 4;

and
$R_1$ amd m are as defined in claim 3.

5. A compound according to claim 4 of formula Ia''':

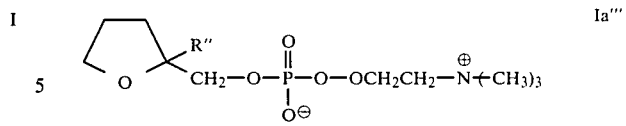

where R" is as defined in claim 4.

6. A compound according to claim 5 having the formula:

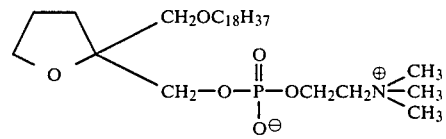

7. A compound according to claim 1 of formula Ib:

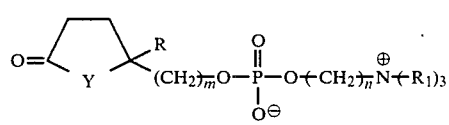

where Y is —O— or —S—; and R, $R_1$, m and n are as defined in claim 1.

8. A compound according to claim 7 of formula Ib':

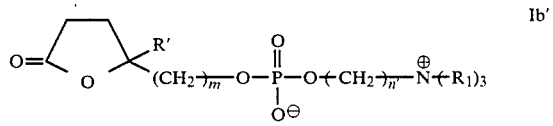

where
- R' is n-$C_{16}$-$C_{18}$ alkyl; $CH_2OR'_2$, where $R'_2$ is n-$C_{16}$-$C_{18}$ alkyl; or $CH_2CH_2OR'_2$, where $R'_2$ is as defined above;
- n" is as integer 2 to 6;

and
$R_1$ and m are as defined in claim 7.

9. A compound according to claim 8 of formula Ib":

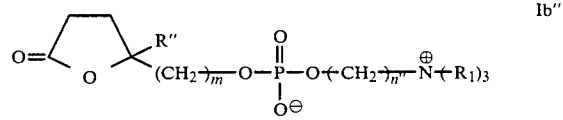

where
- R" is n-$C_{16}$-$C_{18}$ alkyl or $CH_2OR'_2$, where $R'_2$ is as defined in claim 8;
- n" is an integer 2 to 4;

and
$R_1$ and m are as defined in claim 8.

10. A compound according to claim 9 of formula Ib''':

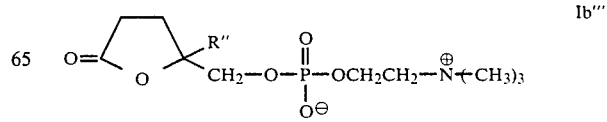

where R″ is as defined in claim 9.

11. A compound according to claim 10 having the formula

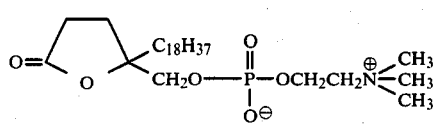

12. A compound according to claim 1 of formula Ic:

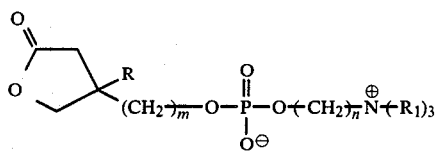

where R, R₁, m and n are as defined in claim 1.

13. A compound according to claim 12 of formula Ic′:

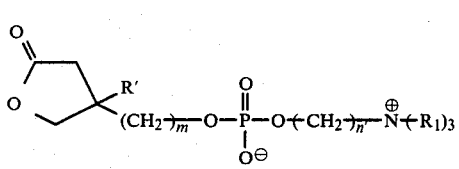

where
R′ is n-C$_{16}$–C$_{18}$ alkyl; CH$_2$OR′$_2$, where R′$_2$ is n-C$_{16}$–C$_{18}$ alkyl; or CH$_2$CH$_2$OR′$_2$, where R′$_2$ is as defined above;
n′ is an integer 2 to 6;
and
R$_1$ and m are defined in claim 12.

14. A compound according to claim 13 of formula Ic″:

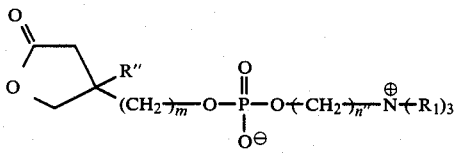

where
R″ is n-C$_{16}$–C$_{18}$ alkyl or CH$_2$OR′$_2$, where R′$_2$ is as defined in claim 13;
n″ is an integer 2 to 4;
and
R$_1$ and m are as defined in claim 13.

15. A compound according to claim 14 of formula Ic‴:

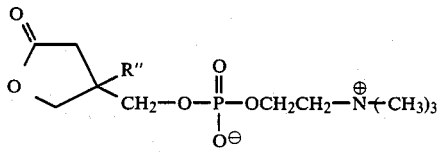

where R″ is as defined in claim 14.

16. A compound according to claim 15 having the formula

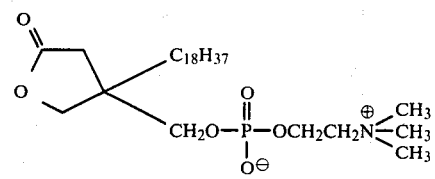

17. A compound according to claim 1 of formula Id:

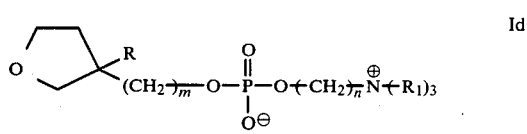

where R, R₁, m and n are as defined in claim 1.

18. A compound according to claim 17 of formula Id′:

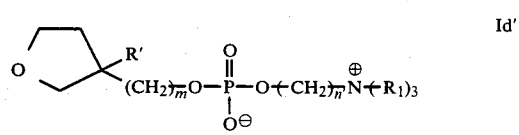

where
R′ is n-C$_{16}$–C$_{18}$ alkyl; CH$_2$OR′$_2$, where R′$_2$ is n-C$_{16}$–C$_{18}$ alkyl; or CH$_2$CH$_2$OR′$_2$, where R′$_2$ is as defined above;
n′ is an integer 2 to 6;
and
R$_1$ and m are as defined in claim 17.

19. A compound according to claim 18 of formula Id″:

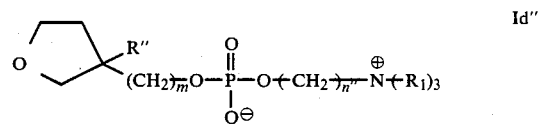

where
R″ is n-C$_{16}$–C$_{18}$ alkyl or CH$_2$OR′$_2$, where R′$_2$ is as defined in claim 18;
n″ is an integer 2 to 4;
and
R$_1$ and m are as defined in claim 18.

20. A compound according to claim 19 of formula Id‴:

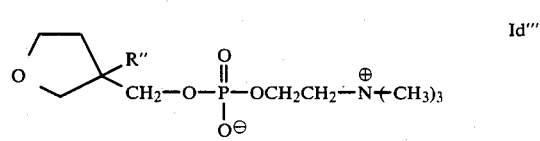

where R″ is as defined in claim 19.

21. A compound according to claim 20 having the formula

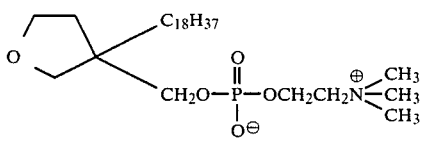

22. A method of treating tumors comprising administering to a subject afflicted therewith a therapeutically effective amount of a compound according to claim 1.

23. A method according to claim 22 comprising administering to a mammal in need of such treatment a therapeutically effective amount of the compound of the formula

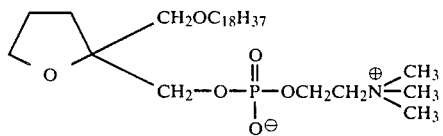

24. A method according to claim 22 comprising administering to a mammal in need of such treatment a therapeutically effective amount of the compound of the formula

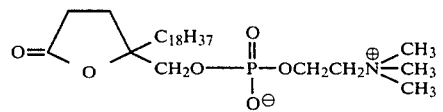

25. A pharmaceutical composition useful in treating tumors comprising a pharmaceutically acceptable carrier and a therapeutically effective amount of a compound according to claim 1.

* * * * *